United States Patent [19]

Phillips et al.

[11] Patent Number: 5,077,258

[45] Date of Patent: Dec. 31, 1991

[54] VAPOR DEPOSITED METAL CATALYTIC FILM, PROCESS FOR MAKING THE SAME AND LIQUID CONTAINER WITH THE FILM

[75] Inventors: Roger W. Phillips; Lauren R. Wendt, both of Santa Rosa, Calif.

[73] Assignee: Flex Products, Inc., Santa Rosa, Calif.

[21] Appl. No.: 538,570

[22] Filed: Jun. 15, 1990

[51] Int. Cl.⁵ .................. B01J 23/28; B01J 23/42; B01J 23/44; B01J 23/74

[52] U.S. Cl. ...................... 502/321; 502/337; 502/338; 502/339; 220/454

[58] Field of Search .............. 502/321, 337, 338, 339; 220/454

[56] References Cited

U.S. PATENT DOCUMENTS

| | | | |
|---|---|---|---|
| 3,944,504 | 3/1976 | Ford et al. | 502/527 X |
| 3,957,692 | 5/1976 | Cairns et al. | 502/314 |
| 4,536,482 | 8/1985 | Garcia | 502/332 X |
| 4,883,782 | 11/1989 | Brown et al. | 502/527 X |

Primary Examiner—W. J. Shine
Attorney, Agent, or Firm—Flehr, Hohbach, Test, Albritton & Herbert

[57] ABSTRACT

Metal catalytic film comprising a flexible substrate having a surface, a catalytic metal layer adherent to said surface of the substrate and having a thickness ranging from 200 to 1000 Angstroms.

Method for forming metal catalytic film on a flexible substrate having a surface in a vacuum chamber comprising the steps of evacuating the vacuum chamber to a predetermined vacuum, introducing a substantially inert heavy gas into the vacuum chamber, creating a vapor stream of molecules of a catalytic metal in the vacuum chamber whereby the molecules of the catalytic metal are scattered by the inert heavy gas and are subsequently deposited upon the surface of the substrate to form a catalytic metal layer to a thickness ranging from 200 to 1000 Angstroms.

16 Claims, 4 Drawing Sheets

VAPOR DEPOSITED METAL CATALYTIC FILM, PROCESS FOR MAKING THE SAME AND LIQUID CONTAINER WITH THE FILM

This invention relates to a vapor deposited metal catalytic film, a process for making the same and a liquid container containing the same to be used in connection with cleaning and disinfecting contact lenses.

At least two types of contact lens disinfecting and cleaning solutions are available in the marketplace. One is based on a hydrogen peroxide solution and the other is based on a chlorite solution. Both utilize a catalyst which is formed by electrodepositing platinum onto a gear-shaped substrate from a chloroplatinate solution. It has been found there have been a number of disadvantages in providing a catalyst of this type. The resulting product is bulky and the coating has low adhesion. It may also contain impurities which are introduced from the electrolyte used in the electrodeposition process. Also, there is a lack of desired uniformity in the reactivity of the deposited catalyst. In addition, there have been difficulties in reclaiming the platinum in the spent solutions and disposing of the electrolytes. There is therefore a need for an improved metal catalytic film and a process for making the same.

In general, it is an object of the present invention to provide a metal catalytic film, a process for making the same and a liquid container which contains the metal catalytic film.

Another object of the invention is to provide a metal catalytic film which has been vapor deposited.

Another object of the invention is to provide a vapor deposited metal catalytic film which has a uniform thickness.

Another object of the invention is to provide a film of the above character which can be produced in a continuous process.

Another object of the invention is to provide a process which is capable of preparing large areas of the film in a uniform manner.

Another object of the invention is to provide a film of the above character which can be deposited on thin polymeric films in roll form.

Another object of the invention is to provide a process of the above character which is a dry process and thereby eliminates the need for disposal of electrolytes and cleaning washes.

Another object of the invention is to provide a container which has a metal catalytic film incorporating the present invention carried therein.

Additional objects and features of the invention will appear from the following description in which the preferred embodiments are set forth in detail in conjunction with the accompanying drawings.

In general, the metal catalytic film of the present invention comprises a flexible substrate having a surface. A catalytic metal layer is adherent to the surface of the substrate and can have a thickness ranging from 200 to 1000 Angstroms. A catalytic metal layer is characterized in that it is porous and has a silvery gray to black color. The substrate is preferably one in which the surface area exceeds its geometrical area, e.g., one that has a rough surface. The rough surface can be characterized as having an Ra value of 0.05 to 0.7 microns. The metal layer is also characterized in that it is of high purity in the range of approximately 99.9%. The catalytic metal can be selected from the group of platinum, palladium, molybdenum, nickel and iron.

In the method for forming the metal film, a flexible substrate having surfaces is provided in the vacuum chamber. The vacuum chamber is evacuated to a predetermined vacuum and thereafter a substantially inert heavy gas is introduced into the vacuum chamber to create a lower vacuum ranging from $2.5 \times 10^{-1}$ to $5 \times 10^{-3}$ Torr. A vapor stream of the catalytic metal is created in the vacuum chamber which impinges upon the surface of the substrate to form a catalytic layer having a thickness ranging from 200 to 1000 Angstroms. The catalytic metal is evaporated by use of a electron beam or, alternatively, by sputtering.

A liquid container is provided for utilizing the catalytic metal film of the present invention. The metal catalytic film is disposed around the inner perimeter of the container.

Figure 1:
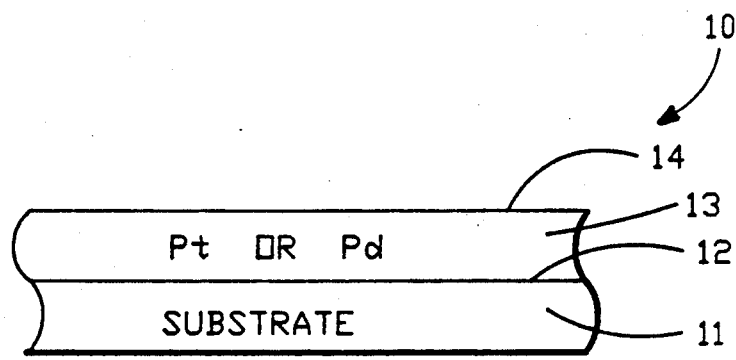
FIG. 1 is a cross sectional view showing a cross section of a metal catalytic film incorporating the present invention.

More particularly, as shown in FIG. 1, there is provided a vapor deposited metal catalytic film 10 which is comprised of a substrate 11 formed of a suitable flexible non-metallic material such as plastic which is provided with a surface 12. In order to increase the surface area, the surface 12 preferably should be textured in a suitable manner to increase catalytic activity as hereinafter described. The texturing of the surface 12 can be accomplished in a conventional manner such as by chemical etching, by embossing and the like.

As soon as an appropriate textured surface 12 has been provided, a layer 13 of a catalytic metal having a surface 14 is deposited upon the surface 12. The metal is deposited to a thickness of 200 to 1000 Angstroms and since it is to be a catalytic metal, it must be very pure in the range of substantially 99.9% purity. Two catalytic metals found to be particularly satisfactory for deposition in a high pressure vacuum deposition process are platinum and palladium. Other typical catalysts also can be used such as molybdenum, nickel and iron. The vacuum deposition process is carried out in a high vacuum ranging from $2.5 \times 10^{-1}$ to $5 \times 10^{-3}$ Torr. Greater uniformity of deposit of the metal is obtained by utilizing a high vacuum deposition process rather than solution chemistry.

Figure 2:
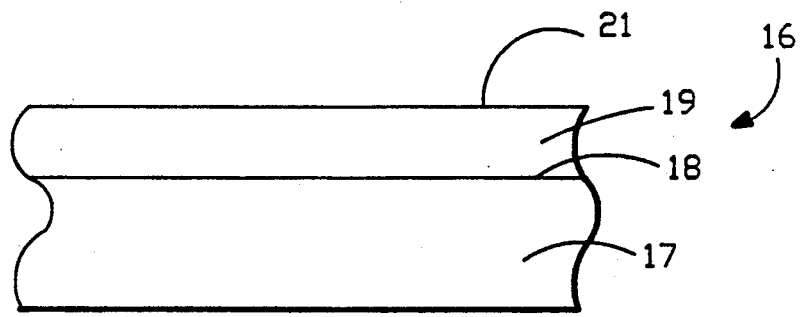
FIG. 2 is a cross sectional view similar to FIG. 1 but showing a specific construction of the film.

A more specific embodiment of a film 16 incorporating the present invention is shown in FIG. 2 in which the film is comprised of a substrate 17 formed of a suitable plastic material. One suitable plastic material is a polyester identified as ICI 377 sold under the trademark "Melinex". It is provided with a translucent matte finish having a medium surface gloss. It can have a suitable thickness such as 142 gauge. Another product which has been found to be satisfactory is Reflexite which is another polyester, on which there is deposited an acrylic layer which is then either embossed or ultraviolet cured to form a corner cube pattern to thereby provide a roughness which increases the effective surface area of the surface 18. A layer 19 of a catalytic metal such as platinum is deposited on the surface 18 to a suitable thickness as, for example, approximately 800 Angstroms and has a surface 21. The surface 21 is porous and provides an increase in surface area. In the preparation of the film shown in FIGS. 1 and 2, it is desirable that there be good adherence between the catalytic metal and the substrate to prevent easy removal of the deposited metal from the surface 18.

Figure 3:
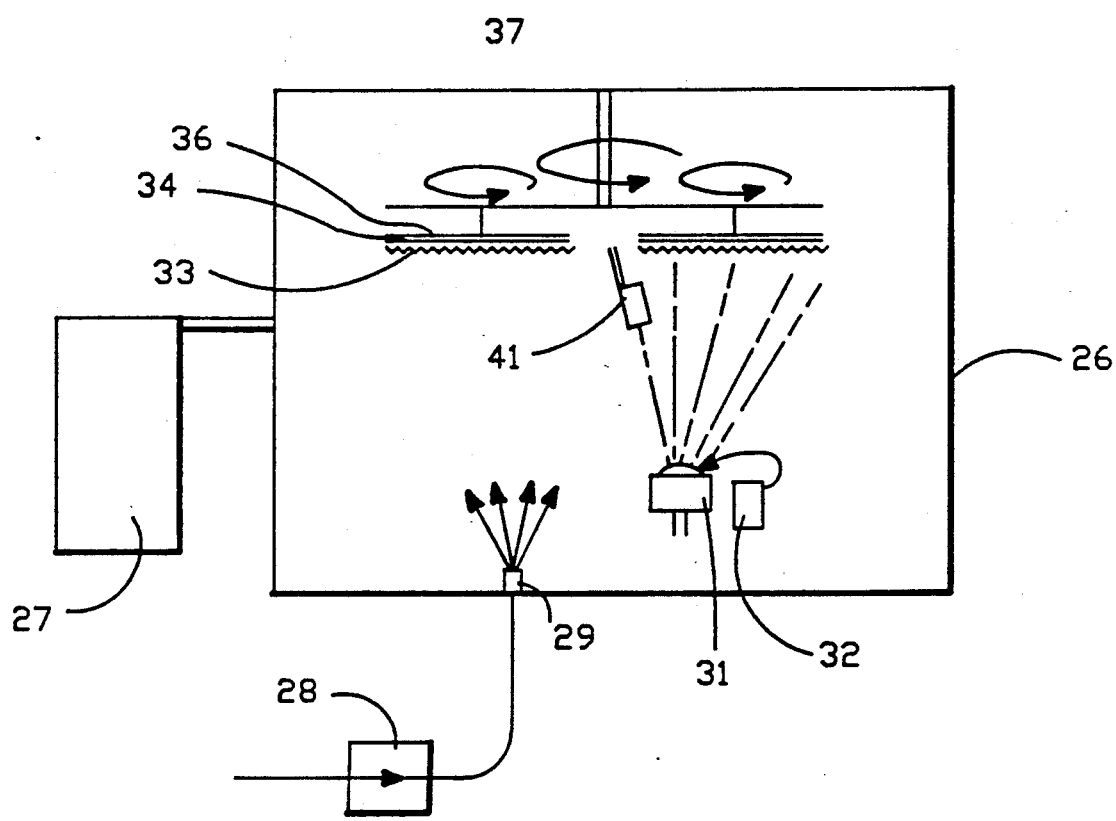
FIG. 3 is a drawing schematically illustrating the manner in which the metal catalytic film can be formed in a batch coater.

In FIG. 3 there is shown a batch coater which can be utilized for performing the method in manufacturing the vapor deposited metal catalytic film of the present invention. It consists of a vacuum chamber 26 of a conventional type which is evacuated by the use of vacuum pumps to a suitable vacuum as, for example, $10^{-5}$ Torr. The vacuum chamber is supplied with a suitable inert heavy gas such as Argon through a regulator 28 and into a inlet 29 provided in the chamber. A water cooled crucible 31 is provided within the chamber and filled with a suitable catalytic metal, as for example, platinum. The platinum is adapted to be evaporated by an electron beam gun 32 as shown in FIG. 3 to provide a vapor stream. The evaporated platinum is deposited onto a plastic substrate of a type hereinbefore described. Typically, the plastic can be cut into 10" squares which can be taped to metal plates 34 of a suitable material such as aluminum. The metal plates 34 are then secured to a substrate holder 36 which is rotatably mounted upon a rotating arm assembly rotatably mounted within the vacuum chamber 26 to provide a double rotation rotary motion to the plastic squares 33. Such a double rotation system is described in U.S. Pat. No. 3,617,331. The amount of catalytic metal deposited on the plastic squares is monitored by a conventional crystal monitor 41 mounted within the chamber adjacent the double rotation system. The double rotating system which is utilized provides the desired uniformity in the catalytic metal which is deposited on the plastic film.

In operating the batch coater shown in FIG. 3 to produce the metal catalytic film of the present invention, the chamber 26 is evacuated to a suitable vacuum such as $10^{-3}$ to $10^{-5}$ Torr. A heavy inert gas such as argon gas is then introduced into the chamber to a pressure for the heavy inert gas ranging from $10^{-3}$ to $10^{-1}$ Torr and preferably approximately $1 \times 10^{-2}$ Torr of mercury as measured on a vacuum pressure gauge. The argon gas is utilized to scatter the platinum molecules in the vapor stream as they evaporate from the crucible 31. The collisions with the argon gas slow down the platinum molecules which causes them to lose energy and to scatter before they arrive at the plastic squares or substrates 33. Typically in such a vacuum chamber, a shutter is used to cover the crucible until the crucible gets up to temperature and the platinum starts evaporating. As soon as the evaporative state is reached by the platinum metal, the shutter is opened and the coating of the plastic film substrate monitored by the crystal monitor 41. As soon as the thickness on the crystal monitor reaches a predetermined thickness, as for example, approximately 800 Angstroms, the shutter is closed and the electron gun is turned off. The valves are closed to shut off the flow of Argon gas into the chamber until all of the argon gas has been pumped out of the chamber and a vacuum $10^{-5}$ Torr has been reestablished. The chamber is then permitted to cool for a suitable period of time, as for example, approximately 15 minutes, after which the chamber 26 can be vented and the coated plastic film can be removed.

In the event that additional 10 inch squares are desired to be coated, the same steps are repeated in the coater. Other heavy inert gases can be utilized in the place of argon if desired. For example, krypton, xenon and possibly, nitrogen would be suitable gases. The gas should be a non-reactive gas and should be capable of causing scattering. By utilizing such a heavy gas in the process, and causing extensive scattering of the platinum molecules in the vapor stream, the metal, when it is deposited on the squares 33 provides a porous structure. Care must be taken in introducing the gas so that the metal which is deposited will adhere as a continuous film. It should not be so porous so as to be almost like dust permitting it to be readily removed.

The entire coating process in the vacuum chamber 26 is carried out at room temperature. The only heat which is generated is that which is created during the evaporation of the metal by the electron beam gun.

It should be appreciated that in place of the electron beam gun which is utilized for evaporating the metal in the batch coater 26 shown in FIG. 3, that a magnetron sputtering device can be utilized for knocking off platinum molecules or atoms from the platinum metal to provide a vapor stream, rather than utilizing an electron beam gun to evaporate the platinum. However, when utilizing a sputtering process, the distance between the source and the substrate to be coated is much less, as for example, approximately two inches, rather than the approximately 20 inches utilized when the electron beam gun evaporation is utilized. In addition, in the sputtering process, the pressure of Argon gas is, for example, $10^{-1}$ Torr. It should be appreciated that $10^{-1}$ Torr is a much higher pressure that what is normally used for D.C. magnetron sputtering. Normal D.C. magnetron sputtering processes use an Argon pressure of about $10^{-3}$ Torr and such pressures result in non-porous shiny metal surfaces.

Sputtering is desirable because it is more efficient in the use of material. The only material which is utilized goes directly to the substrate. Utilizing an electron beam gun for evaporation, the platinum metal is evaporated into a wide stream in accordance with a cosine distribution so that the interior of the chamber is coated as well as the substrate. Sputtering has a disadvantage in that it is slower. The sputtering process is more controllable which makes it possible to provide coatings of a given thickness based upon time and rate. This is difficult to achieve by electron beam evaporation and it is for that reason, a monitor is utilized with electron beam evaporation to ascertain the thickness of the material deposited.

Figure 4:
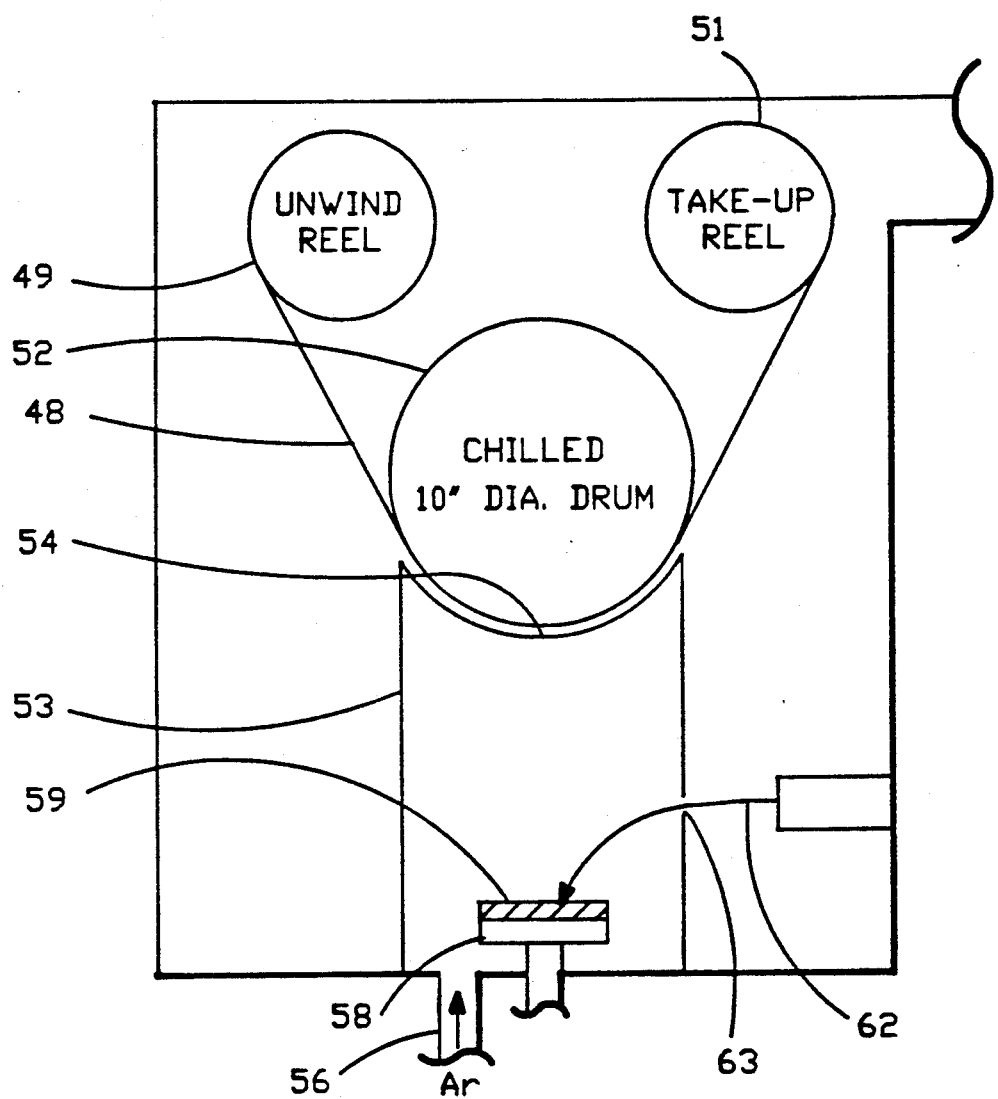
FIG. 4 is a schematic illustration of a roll coater which can be utilized for forming the metal catalytic film utilizing electron beam evaporation.

In FIG. 4, there is provided a roll coater which can be utilized for electron beam evaporation of the catalytic metal. The roll coater, as shown, is comprised of a vacuum chamber 46 which is provided with an outlet 47 which can be connected to a conventional vacuum pump so that the chamber 46 can be pumped down to a suitable pressure such as $5 \times 10^{-3}$ Torr. The plastic substrate or web 48 which is to be coated is provided on an unwind reel 49 disposed within the chamber 46 and is taken up by a take-up reel 51, also disposed within the chamber 46. The plastic substrate travels under a chilled drum 52 of a suitable diameter such as 10 inches. The plastic substrate 48 can have a suitable width ranging from 10 to 48 inches. The chilled drum 52 is provided with capabilities for maintaining the same chilled to a temperature of approximately $-20°$ C. from refrigeration equipment (not shown) external of the chamber 46 and connected to the drum by suitable piping.

A rectangular high pressure containment vessel 53 is provided which has an arcuate upper extremity 54 that conforms to the cylindrical surface of the drum 52. The containment vessel is provided with an inlet 56 through which a suitable inert heavy gas such as argon can be supplied to maintain a high pressure as, for example, approximately $10^{-2}$ Torr. A crucible 58 of a suitable type such as a coated copper crucible is provided at the bottom of the containment vessel and carries the catalytic metal 59 which can be of a suitable type such as platinum. An electron gun 61 is mounted within the chamber 46 and provides a trajectory of electrons 62 which pass through an opening 63 provided in the containment vessel to impinge upon the metal 59 to create a vapor stream of platinum molecules within the containment vessel 53.

In operation of the roll coater shown in FIG. 4, the electron beam evaporates the catalytic metal 59 to provide a high pressure cloud of catalytic metal molecules in the pressure containment vessel 53. The scattered molecules impinge upon one surface of the substrate 48 passing under the chilled drum 52 to provide a porous catalytic metal on the surface of the substrate 48 having a suitable thickness ranging from 200 to 1000 Angstroms and preferably a thickness of about 800 Angstroms. When platinum or palladium is utilized as the catalytic metal and is porous as desired in the present invention, it has a dark gray or almost black appearance.

Figure 5:
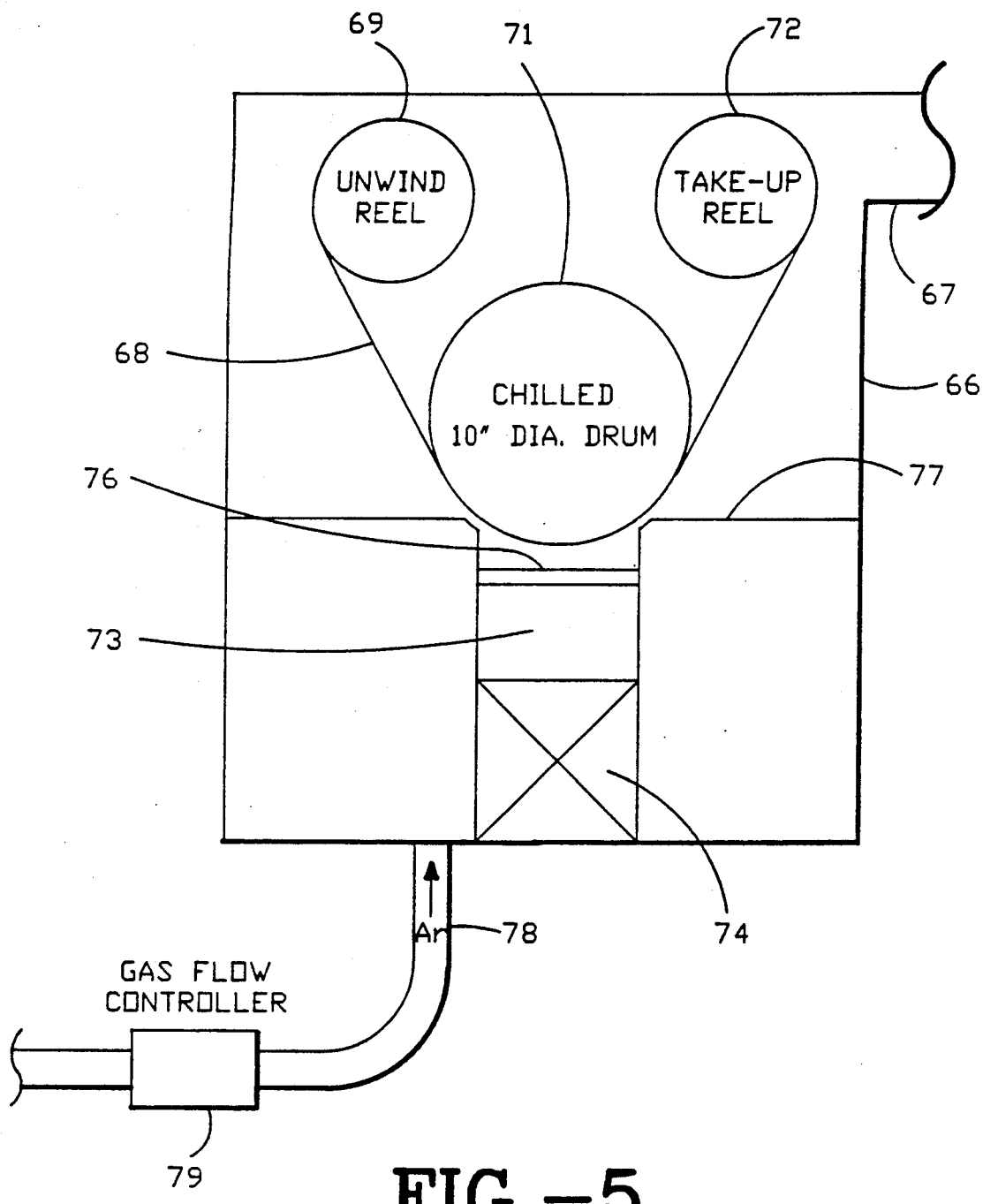
FIG. 5 is a schematic illustration of a roll coater which can be utilized for depositing the metal catalytic film by magnetron sputtering.

In FIG. 5, there is shown a roll coater with magnetron sputtering. It is comprised of a vacuum chamber 66 which is provided with an outlet 67 connected to a suitable vacuum pumping station to provide a high vacuum of approximately $5 \times 10^{-5}$ Torr. The plastic substrate or web 68 to be coated of the type hereinbefore described is carried by an unwind reel 69 provided in the chamber 66 and passes under a chilled 10" drum 71 in the chamber 66 and is picked up by a takeup reel 72 also mounted within the chamber 66. A magnetron sputtering device 73 is mounted in the chamber upon a pedestal 74. A metal target 76 of a suitable catalytic metal such as platinum is mounted upon the magnetron sputtering device 73. A mask 77 is provided within the vessel so that the sputtered molecules generated in the sputtering process are directed across a rectangular region below the bottom of the chilled drum 71 extending across the plastic web 68. The sputtering process has advantages in that the magnetron will operate in the low pressure required without problems unlike the electron beam process which is prone to arcing. Also in the sputtering process, the precious platinum metal is merely directed towards the bottom of the drum 71, rather than throughout the chamber 66 as is the case with electron beam evaporation. In electron beam evaporation, approximately 8 to 10% of the metal is deposited onto the plastic substrate or web underlying the drum and in the case of sputtering approximately 50% of the metal is deposited onto the plastic substrate.

Typically, the plastic web 68 could have a suitable width, as for example, 10" and can be advanced in the chamber at a suitable speed to obtain a catalytic metal deposited on the plastic having a thickness ranging from 200 to 1000 Angstroms and preferably a thickness of approximately 800 Angstrom and to give an appearance of almost black or a blackish gray appearance which can be characterized as a silvery-gray to black appearance because of the porosity made possible by evaporating or sputtering the platinum in the presence of a heavy or inert gas.

The heavy gas is introduced through an inlet 78 provided in the chamber 66 through a gas flow controller 79 of a conventional type. In connection with the present invention, it has been found that it is possible to provide a very black metal film which still has the desired adhesion to the substrate. Typically, the sputtering process is preferred because it is possible to control the thickness of the deposit more accurately across the width of the plastic web. Sputtering also eliminates the need for complicated masking.

It is desirable that the metal catalytic coating have adhesion to the substrate which is sufficient to prevent it from being removed by wiping a finger across the same. It is also desirable that when the metal catalytic film when used in a liquid such as a saline solution remains intact and will not come loose for substantial periods of time as, for example, in excess of 3 months. It also should be crinkle resistant.

Typically in the past it has been the practice to evacuate metals in the best possible vacuum to obtain good specular films with good adherence whether or not sputtering or electron beam evaporation is utilized. In the present invention by utilizing low vacuums (i.e. high pressures), rather than high vacuums and utilizing an inert heavy gas to create scattering, a porous film or coating of catalytic metal is provided on the substrate which has good adherence.

The porosity which can be achieved in the present invention has pore dimensions of 10 to 100 Angstroms and preferably 50 to 100 Å.

Figure 6:
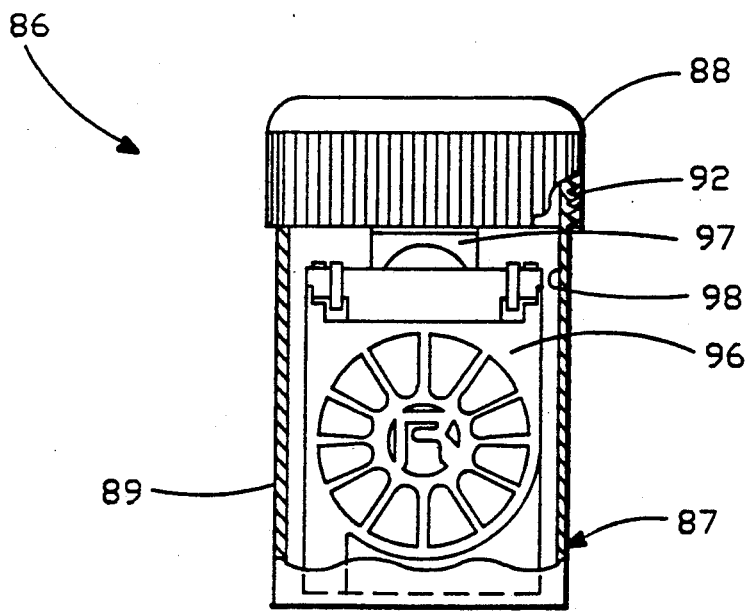
FIG. 6 is an isometric view, partially cut away, of a container which carries the metal catalytic film of the present invention.

A liquid container 86 for utilizing a vapor deposited metal catalytic film of the present invention is shown in FIG. 6. As shown therein, it is comprised of a receptacle 87 and a screw on cap 88. The receptacle is provided with a cylindrical side wall 89 and a flat bottom wall 91. The upper end of the receptacle 87 is open and is provided with threads 92 which are adapted to mate with threads (not shown) on the interior of the cap 88. A lens container assembly 96 is mounted on the cap 88 and is suspended therefrom by a post 97 so that it is centrally disposed within the interior of the receptacle 87. The lens container assembly 96 is of a conventional type and is provided with openable spaces therein which are adapted to receive the right and left contact lenses of a person. The receptacle 87 can be formed of a suitable transparent plastic and the cap can be formed of opaque plastic such as white plastic. The lens container assembly 96 can be formed of the same material as the cap.

A strip or film 98 of vapor deposited metal catalytic film of the present invention is disposed within the interior of the receptacle 87 and has a width as shown which extends approximately ⅔ the height of the container and extends around the entire inner perimeter of the receptacle 87. The strip or film 98 is thus disposed adjacent the side wall of the receptacle 87 in a position substantially parallel to the side wall 89. It has been found that the strip 98 has enough rigidity so that it will remain in contact with the side wall 89 without the use of an adhesive. The strip 98 can be cut to a length so that the ends abut each other within the container.

However, if desired, the strips can be cut so that the ends overlap.

In using the liquid container 86, the container can be filled with the desired liquid to a desired level within the container, as for example, to the top of the strip 98 provided in the container. The lenses can then be inserted into the lens container assembly 86 for cleaning and disinfecting in a conventional manner in which the metal catalytic film acts as a catalyst. If the container is filled with a chlorite saline solution, the platinum black catalyst carried by the strip is used to change chlorite to chlorine dioxide which disinfects the contact lenses carried in the contact lens assembly.

The plastic lens container assembly 96 permits the liquid in the container to flow freely through the assembly to come in contact with the contact lenses so that it can be used for an hour or overnight as the user desires.

It has been found that the metal catalytic film made in accordance with the present invention remains intact within the container and does not flake or peel off after extensive use.

What is claimed is:

1. A metal catalytic film comprising a flexible non-metallic substrate having a surface, a porous catalytic metal layer formed of a single material adherent to said surface of the substrate and having a thickness ranging from 200 to 1000 Angstroms.

2. A metal catalytic film as in claim 1 wherein said layer has a silvery gray-to-black color.

3. A metal catalytic film as in claim 1 wherein the metal layer has pores having diameters in the range 10–100 Å.

4. A metal catalytic film as in claim 1 wherein said catalytic metal layer is formed of a metal having a purity of approximately 99.9%.

5. A metal catalytic film as in claim 4 wherein said metal is selected from the group of platinum, palladium, molybdenum, nickel and iron.

6. A method for forming metal catalytic film on a flexible non-metallic substrate having a surface in a vacuum chamber, evacuating the vacuum chamber to a vacuum ranging from $10^{-3}$ to $10^{-5}$ Torr vacuum, introducing a substantially inert heavy gas into the vacuum chamber, creating a vapor stream of molecules of a catalytic metal of a single material in the vacuum chamber whereby the molecules of the catalytic metal are scattered by the inert heavy gas and are subsequently deposited upon the surface of the substrate to form a porous catalytic metal layer to a thickness ranging from 200 to 1000 Angstroms.

7. A method as in claim 6 wherein the vapor stream is formed by electron beam gun evaporation.

8. A method as in claim 6 wherein said vapor stream is formed by sputtering.

9. A method as in claim 6 wherein the pressure of the heavy inert gas in the vacuum chamber ranges from $10^{-3}$ to $10^{-1}$ Torr.

10. A method as in claim 6 wherein the gas introduced is argon.

11. A method as in claim 6 wherein the substrate is advanced through the vapor stream during the time that the vapor stream is impinging upon the surface of the substrate in a continuous process.

12. A method as in claim 6 wherein the substrate is rotated through the vapor stream in a batch process.

13. A liquid container comprising a container having a wall, a catalytic metal film disposed within the container adapted to be contacted by liquid introduced into the container and a cap for closing the container.

14. A container as in claim 13 wherein said container is provided with a side wall and wherein said catalytic film is disposed adjacent the side wall in a position substantially parallel to the side wall.

15. A container as in claim 13 wherein said catalytic film is comprised of a substrate having a layer of a catalytic metal adherent thereto having a thickness ranging from 200 to 1000 Angstroms.

16. A container as in claim 13 wherein said catalytic metal layer is substantially porous and has a silvery gray to black appearance.

* * * * *